(12) United States Patent
Kuusela et al.

(10) Patent No.: US 11,439,843 B2
(45) Date of Patent: Sep. 13, 2022

(54) KNOWLEDGE BASED TREATMENT PLANNING CORRECTED FOR BIOLOGICAL EFFECTS

(71) Applicant: Varian Medical Systems International AG., Cham (CH)

(72) Inventors: Esa Kuusela, Espoo (FI); Jarkko Y. Peltola, Tuusula (FI); Joakim Pyyry, Helsinki (FI)

(73) Assignee: VARIAN MEDICAL SYSTEMS INTERNATIONAL AG, Cham (CH)

( * ) Notice: Subject to any disclaimer, the term of this patent is extended or adjusted under 35 U.S.C. 154(b) by 359 days.

(21) Appl. No.: 16/730,519

(22) Filed: Dec. 30, 2019

(65) Prior Publication Data

US 2020/0147411 A1    May 14, 2020

Related U.S. Application Data

(62) Division of application No. 15/487,284, filed on Apr. 13, 2017, now Pat. No. 10,556,125.

(51) Int. Cl.
*A61N 5/10* (2006.01)

(52) U.S. Cl.
CPC .......... *A61N 5/1031* (2013.01); *A61N 5/103* (2013.01); *A61N 2005/1041* (2013.01)

(58) Field of Classification Search
CPC .............. A61N 5/103–1039; A61N 2005/1041
See application file for complete search history.

(56) References Cited

U.S. PATENT DOCUMENTS

| | | |
|---|---|---|
| 2012/0014507 A1 | 1/2012 | Wu et al. |
| 2013/0077752 A1 | 3/2013 | Zankowski |
| 2014/0378737 A1 | 12/2014 | Carpenter et al. |
| 2017/0259082 A1 | 9/2017 | Bzdusek et al. |
| 2017/0259083 A1 | 9/2017 | Nakatsugawa et al. |
| 2018/0148791 A1 | 5/2018 | Scott et al. |

*Primary Examiner* — Thaddeus B Cox

(57) ABSTRACT

Solutions are provided herein that specifically accounts for biological effects of tissue during radiation planning (such as treatment planning). In one or more embodiments, the biological effects may be calculated by accessing a knowledge base to determine reference data comprising at least one biological characteristic corresponding to the at least one organ, predicting a biological effect for the plurality of identified structures based on the biological characteristic corresponding to the at least one organ, and generating or modifying a radiation plan based on the biological effect. By incorporating biological data and fraction dose information, dose-estimation models can be created and trained to more accurately estimate dose absorption and effectiveness. Moreover, existing estimation models may be adapted to create dose estimations that account for the biological efficiency of target structures.

20 Claims, 6 Drawing Sheets

600

KNOWLEDGE BASED TREATMENT PLANNING CORRECTED FOR BIOLOGICAL EFFECTS

CROSS-REFERENCE TO RELATED APPLICATION

This is a divisional application of U.S. patent application Ser. No. 15/487,284 entitled "Knowledge Based Treatment Planning Corrected for Biological Effects," by Esa KUUSELA et al., filed Apr. 13, 2017, now U.S. Pat. No. 10,556,125, which is hereby incorporated by reference.

TECHNICAL FIELD

Embodiments of this invention relate generally to directed irradiated particle beam applications. More specifically, embodiments of this invention are directed to improved methods and systems for limiting a beam of irradiated particles to achieve a target dosage.

BACKGROUND OF THE INVENTION

Radiology is the branch of medical science dealing with medical imaging for the purpose of diagnosis and treatment. The practice of radiology often involves the usage of X-ray machines or other radiation devices to perform the diagnosis or administer the treatment. Other practices of radiology employ techniques that do not involve radiation, such as magnetic resonance imaging (MRI) and ultrasound. Within the medical field, radiology can refer to two sub-fields, diagnostic radiology and therapeutic radiology. Diagnostic radiology is concerned with the use of various imaging modalities to aid in the diagnosis of disease or condition. Therapeutic radiology or radiation oncology uses radiation to treat diseases such as cancer through the application of radiation to targeted areas.

In diagnostic radiology, a typical configuration for a radiology device includes a radiation source used to emit the irradiating particles (e.g., X-rays) and one or more imaging devices corresponding to the radiation source. The particles are directed towards a target volume (i.e., a patient) situated between the source and imaging device(s), with the imaging device(s) being positioned to collect incoming radiation that passes through the target volume. The beams collected by the imagers are subsequently used to generate one or more images of the targeted volume. In radiation therapy, accurately identifying and delineating anatomic structures during the treatment planning phase is critically important. The objective of every such procedure is to provide an accurate definition of a target volume and any organs at risk in order to deliver the maximum radiation dose to the target volume (e.g., tumor) while sparing the surrounding healthy tissue from being subject to exposure to potentially harmful radiation.

During the planning stage, a planner often defines specific structures used to control the dose distribution during treatment optimizations. Typically, these structures are Boolean combinations of targets and normal tissues. By defining the intersection of targets and normal tissues as separate structures, different prescription doses and constraints can easily be applied to different regions, facilitating the creation of controlled dose gradients between normal tissues and targets.

In biological radiation planning, planning metrics are typically expressed according to the biological effect of the irradiation. In contrast, in traditional (non-biological) radiation planning, the measure of an absorbed radiation dose is typically expressed as a physical quantity that does not take into account biological context. The lack of biological context when considering the application of an absolute dose becomes an issue when the effects inherent to radiation application in different fraction doses need to be summed together or compared with each other. Recently, this problem has become more prevalent, since an increasing number of radiation subjects (e.g., treatment patients) are receiving second or even third radiation therapy treatments with possibly varying fraction doses. Furthermore, new hypofractionations used in Stereotactic Body Radio therapy (SBRT) or Stereotactic Radio Surgery (SRS) are using much higher fraction doses than heretofore conventional treatments, making any non-linear effects caused from the biological effect of fraction dose (or the time between individual treatment sessions) more prominent.

The biological efficiency of a radiation dose is known to depend on the fraction dose (non-linear), treatment modality, energy, or even dose rate. In addition, different structures have different recovery rates from the delivered radiation dose. Also, other patient specific factors (e.g., background information, additional anatomical or functional information from PET scanning, response to previous treatments, etc.) can affect the predicted biological effect of certain amounts of dose.

One model that is commonly used to approximate the dependency between a biological effect and the dose delivered to tissue during a single fraction is the Linear-Quadratic (LQ) model, which takes into account non-linear effects due to the recovery rate of a structure. However, the LQ model does not take into consideration that the recovery rate may be different for different types of tissues. When treatments using different fraction doses are compared, it is common to convert the doses to a dose that would provide equal biological effect.

Unfortunately, in current DVH estimation techniques, these biological effects—such as different tissue recovery rates—are not taken into account. Typically, the total dose is considered just as a general scalar value of the dose distributions, and the fraction dose does not play a role at all in the calculation. Moreover, even if the treatment planner has accounted for the biological effect of different fractionations during the planning of the training set plans, current implementations do not properly account for the possibility that the planning goals are functions of the used fraction dose.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in conventional radiation application planning, solutions are provided herein that specifically accounts for biological effects of tissue during radiation planning (such as treatment planning). In one or more embodiments, the biological effects may be calculated and factored to make dose-volume histogram (DVH) estimations, 3D dose distributions, or directly achievable target control probability (TCP) and/or normal tissue complication probability (NTCP) estimations. According to various embodiments, the approach is directly applicable for all radiation (treatment) modalities including, but not limited to, protons, electrons, and photons modalities. According to further embodiments, biological properties are also factor into the training of the models (e.g., DVH estimation model, dose distribution model, TCP, and NTCP estimation model) themselves, with the tissue biological properties of each model structure and the fraction dose of each training case plan. The described techniques may also be used to convert existing dose estimation models to utilize biological effects, or to optimize treatment parameters that affect the biological effect (e.g., fractionation scheme).

According to an aspect of the claimed subject matter, a method is provided herein for radiation planning that comprises the steps of: determining, in a radiation plan, a plurality of identified structures of a radiation target, identifying at least one organ from the plurality of identified structures, accessing a knowledge base to determine reference data comprising at least one biological characteristic corresponding to the at least one organ, predicting a biological effect for the plurality of identified structures based on the biological characteristic corresponding to the at least one organ, and generating a radiation plan based on the biological effect. In one or more embodiments, predicting the biological effect may be performed by, for example, calculating an absolute dose distribution from the radiation application plan, determining a fraction dose based on the absolute dose distribution and the plurality of fractionations, and determining the biological effect based on the at least one biological characteristic and corresponding to the plurality of fractionations.

According to other aspects of the claimed subject matter, systems and computer readable media are provided herein that are configured to perform and operable to execute the radiation application planning described above, respectively. According to one or more embodiments, the systems may be equipped with one or more memory devices comprising programmed instructions, one or more network connections communicatively coupled to one or more networked computing devices storing a knowledge base of clinical training data, and one or more processors equipped to execute the programmed instructions and, with reference to the data derived from the communicatively coupled knowledge base, to generate a radiation plan that includes accounting for expected biological effects based at least on a biological characteristic of an identified structure according to the number of fractionations of the radiation application plan.

In addition to generating estimates for an absolute DVH curve for traditional planning schemes, the knowledge-based approach described herein also generates predictions for the biological effect expected in target areas, based on (inter alia) tissue type. For example, the outcome of a DVH estimation algorithm could be LQ-corrected DVH for each structure taken into account user-specified biological parameters (e.g., recovery rate) for each organ in the model. In alternate embodiments, the biological parameters may be pre-determined (e.g., hard-coded), and/or structure-based. The output can also be converted back to an absolute DVH curve by using the fraction dose of the patient case which the DVH estimates are generated for.

BRIEF DESCRIPTION OF DRAWINGS

The accompanying drawings, which are incorporated in and form a part of this specification, illustrate embodiments of the disclosure and, together with the description, serve to explain the principles of the presently claimed subject matter:

DETAILED DESCRIPTION

Figure 1:
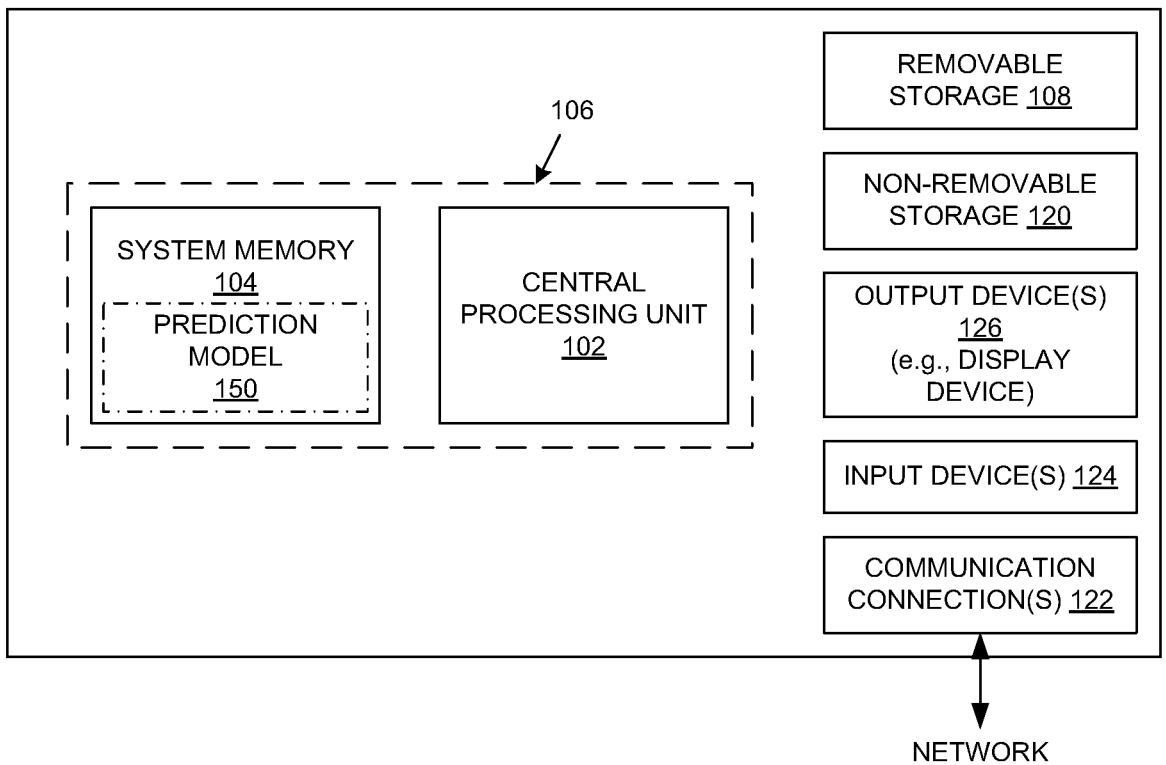
FIG. 1 shows a block diagram of an example of a computing system upon which the embodiments described herein may be implemented.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known processes, procedures, components, and circuits have not been described in detail as not to unnecessarily obscure aspects and features of the subject matter.

Portions of the detailed description that follow are presented and discussed in terms of a process. Although operations and sequencing thereof are disclosed in a figure herein (e.g., FIGS. 4, 5) describing the operations of this process, such operations and sequencing are exemplary. Embodiments are well suited to performing various other operations or variations of the operations recited in the flowchart of the figure herein, and in a sequence other than that depicted and described herein.

Some portions of the detailed description are presented in terms of procedures, operations, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed operation, logic block, process, etc., is here, and generally, conceived to be a self-consistent sequence of operations or instructions leading to a desired result. The operations are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While the following example configurations are shown as incorporating specific, enumerated features and elements, it is understood that such depiction is exemplary. Accordingly, embodiments are well suited to applications involving different, additional, or fewer elements, features, or arrangements.

Exemplary Computing Environment

FIG. 1 shows a block diagram of an exemplary computing system 100 upon which embodiments described herein may be implemented. In its most basic configuration, the system 100 (illustrated in FIG. 1 by dashed line 106) includes at least one processing unit 102, and memory 104. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, (e.g., in a networked environment) using logical connections to one or more remote computers.

According to one or more embodiments, the system 100 may also include input one or more devices 124, such as a keyboard, mouse, pen, voice input device, touch input device, etc. As depicted in FIG. 1, output device(s) 126 such as a display device, speakers, printer, etc., are also included.

As presented in FIG. 1, the memory 104 includes computer-readable instructions, data structures, program modules, and the like associated with a dose prediction model 150. According to alternate embodiments, the dose prediction model 150 may instead (or also) reside in any one of the computer storage media used by the system 100, may be distributed over some combination of the computer storage media, and/or may be distributed over some combination of networked computers.

According to one or more embodiments, the dose prediction model 150 may be used to predict dose parameters for a radiation application plan corresponding to a particular radiation target. The dose prediction model 150 may be implemented as a dose-volume histogram (DVH) estimation model, where the predicted quantity is a dose volume histogram. In other embodiments, the prediction model 150 also generates a prediction based on a distance to a target (DTH) histogram, which expresses the distance from a region of interest (ROI) to a radiation target. In yet other embodiments, the dose prediction model 150 may be implemented as any other model suitable for predicting dosage (as a dose histogram or spatial 3D dose distribution) or estimating probability (e.g., target control probability or normal tissue complication probability) for a radiation application plan.

The dose prediction model 150 can then be used (e.g., by a clinician, a radiologist, and/or an oncologist) to develop a radiation application plan for a particular radiation target. In one or more embodiments, the radiation application plan may be a radiation treatment plan for a radiation therapy patient. According to such embodiments, the dose prediction model may be used to develop a radiation treatment plan by receiving target or patient-specific information (e.g., geometry information) that is input to, and processed by the model. The input information may contain any combination of parameters that can practically affect the radiation treatment plan. For example, the input information may be organized as a vector or a data structure including feature elements for: size and shape of the target volume in the radiation target or patient; location of the target volume; size and shape of an organ at risk; type of an organ at risk; a part of the target volume that overlaps an organ; and a part of an organ that overlaps the target volume.

According to one or more embodiments, the geometry information for a target or patient may include one or more segmented structures. These structures may be manually or automatically determined (e.g., via pre-contouring or other means), and may include at least one organ.

Figure 2:
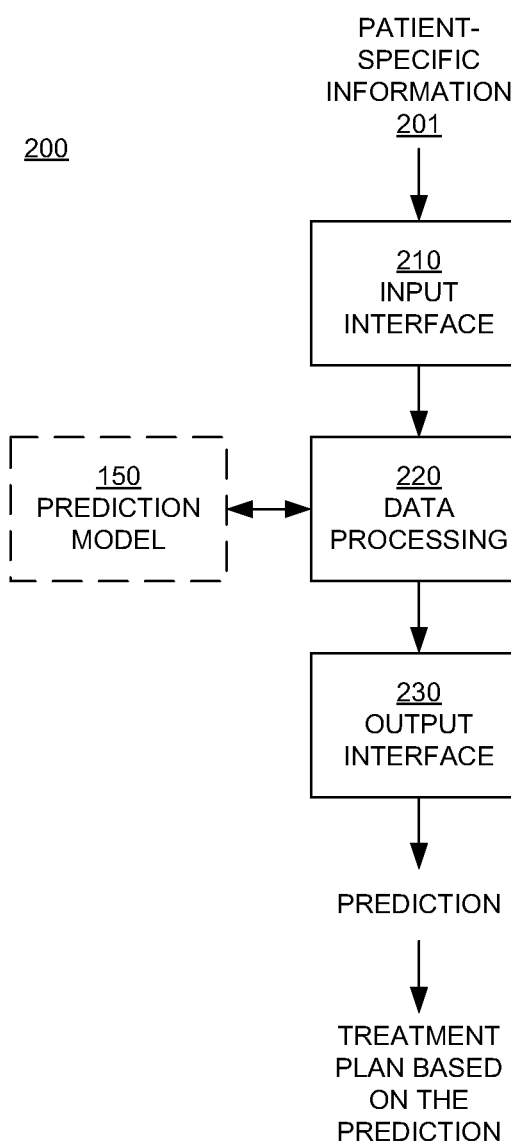
FIG. 2 is a block diagram illustrating an example of an automated radiation treatment planning system in an embodiment according to the present invention.

FIG. 2 is a block diagram illustrating an example of an automated radiation application planning system 200 in an embodiment according to the present invention. In one or more embodiments, the automated radiation application planning system may be implemented to plan radiation therapy treatment plans. The system 200 includes an input interface 210 to receive target or patient-specific information (data) 201, a data processing component 220 that implements the prediction model 150, and an output interface 230. The system 200 in whole or in part may be implemented as a software program, hardware logic, or a combination thereof on/using the computing system 100 (FIG. 1).

The target or patient-specific information is provided to and processed by the prediction model 150. The prediction model 150 yields a prediction result, e.g., an achievable dose distribution prediction. A radiation application or treatment plan based on the prediction result can then be generated, and through a radiation application system, be applied to the radiation target or patient. In an embodiment, the prediction result is accompanied by parameters indicative of the quality of the prediction, such as reliability of the result (e.g., affected by the internal coherence of the training data), complexity of the predicted plan, and probability of the result. According to one or more embodiments, the radiation application or therapy treatment plan may be implemented over a series of radiation application sessions, with the total dose distribution being applied as a plurality of (equal or substantially equal) dose fractionations, with each session corresponding to a dose fraction.

Figure 3:
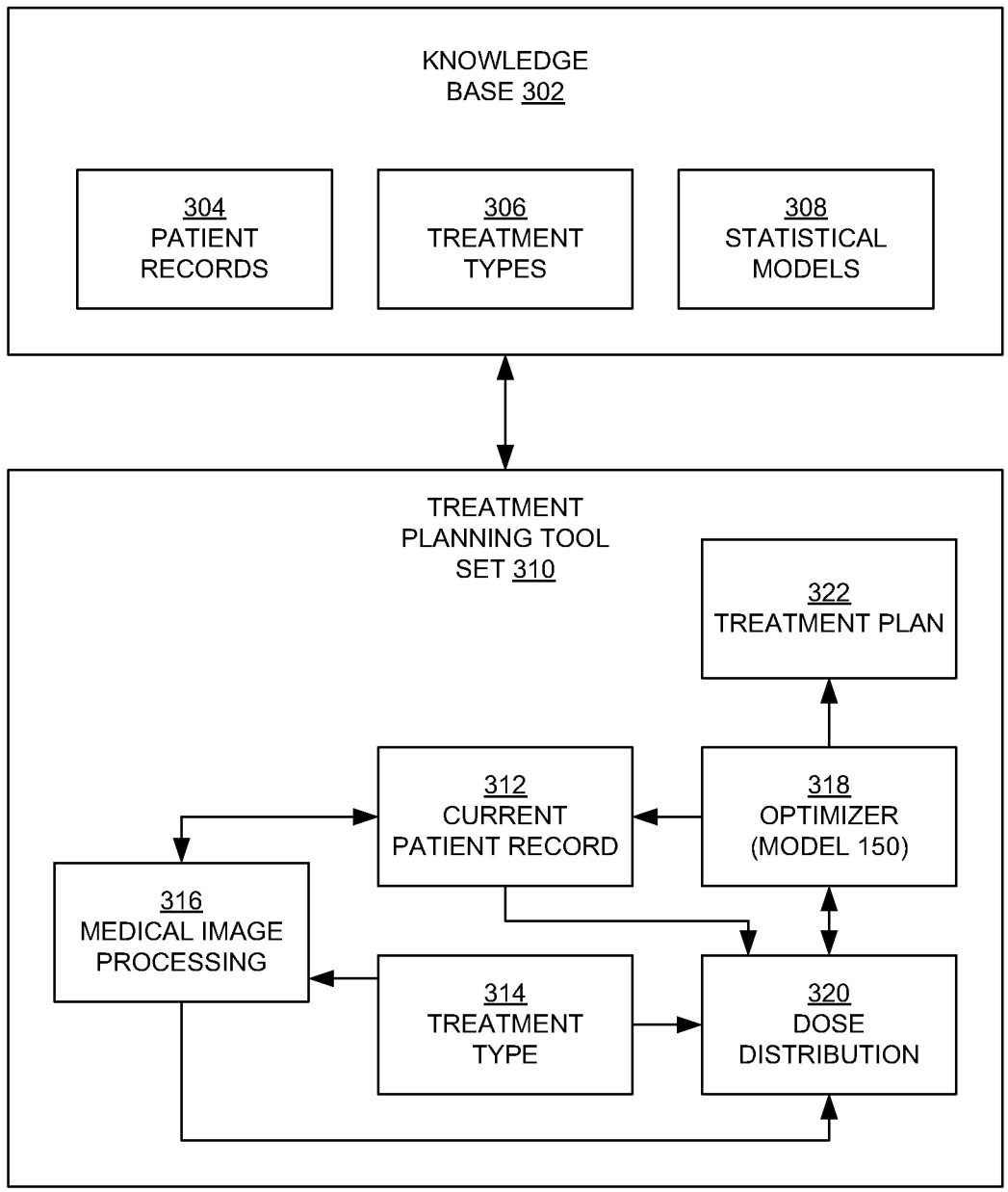
FIG. 3 illustrates an embodiment of a knowledge-based planning system in an embodiment according to the present invention.

FIG. 3 illustrates an embodiment of a knowledge-based planning system 300 incorporating a combination of target or patient records and statistical models for generating radiation application or radiation treatment plans in an embodiment according to the present invention. In the example of FIG. 3, the system 300 includes a knowledge base 302 and a radiation application planning tool set 310. The knowledge base 302 includes previously stored target or patient records 304 (e.g., previously generated radiation treatment plans), application/treatment types 306, and statistical models 308. In one or more embodiments, the previously stored target or patient records may consist of earlier generated medical image and/or segment data or the same target or patient. In addition, the previously stored target or patient records may also consist of previously generated medical image or segment data of other targets or patients that correspond (e.g., include one or more of the same identified structures) to input medical image data of the current radiation target or therapy patient. As depicted, the application/treatment planning tool set 310 in the example of FIG. 3 includes a current target/patient record 312, an application/treatment type 314, a medical image processing module 316, an optimizer 318, a dose distribution module 320, and a final radiation application/treatment plan 322.

The application/treatment planning tool set 310 searches through the knowledge base 302 (through the target or patient records 304) for prior target or patient records that are similar to the current target/patient record 312. The statistical models 308 can be used to compare the predicted results for the current target or patient record 312 to a similar target or patient record. Using the current target or patient record 312, a selected application/treatment type 306, and selected statistical models 308, the tool set 310 generates a radiation application/treatment plan 322.

More specifically, based on past clinical experience, when a target or patient presents with particular parameters (e.g., one or more of a size, diagnosis, stage, age, weight, sex, co-morbidities, etc.) there can be a application or treatment type that is used most often. By selecting the application/treatment type that the planner has used in the past for similar targets or patients, a first-step application/treatment type 314 can be chosen. In one or more embodiments, the medical image processing module 316 provides automatic identification and automatic segmentation of two-dimensional cross-sectional slides (e.g., from computed tomography or magnetic resonance imaging) to form a 3D image using the medical images in the current target or patient record 312. Dose distribution maps are calculated by the dose distribution module 320.

According to one more embodiments, the knowledge base 302 can be referenced for a combination of biological data that can be factored by the optimizer 318 to determine a structure-specific dose distribution that best approximates radiation application or treatment objectives. For example, in one or more embodiments, biological efficiency data for specific structures identified in imaging data corresponding to structures at risk during a radiation application or therapy session is referenced from knowledge base 302. The biological efficiency data may consist of, but is not limited to, alpha/beta parameters in LQ models, tissue type and/or radiation recovery rates per type of tissue. Other reference data may include (but are not limited to) structure-specific repopulation rates, re-distribution rates, re-oxygenation rates, and/or radio resistance rates.

In embodiments according to the present invention, the optimizer 318 uses the dose prediction model 150 to help shape the dose distribution with the biological efficiency data. For example, for a radiation treatment plan of 20 Gys distributed over 10 sessions at 1 session per week, the absolute dose distribution received by the tissue may actually be appreciably less than the 20 Gys due to the biological efficiency and recovery potential of the target structures in between sessions. Thus, to achieve a planned 20 Gy dose distribution, the radiation plan can be adjusted (e.g., by increasing the dosage) to account for the biological effects of the tissue specifically for the fractionation scheme (in this case, 1 session per week over 10 weeks). By referencing clinical data of biological effect data observed in similar statistical models, biological parameters that account for the biological effects can be effectively accounted to more effectively achieve optimal dose distribution.

Accordingly, the optimizer 318 can provide a 3D dose distribution, fluences, and associated dose-volume histograms for the current radiation target or patient. By using the dose prediction model 150, which is trained and validated as described above, those results are expected to fall within the historically accepted range for a patient with a similar disease type and treatment type.

Radiation Application Planning

Figure 4:
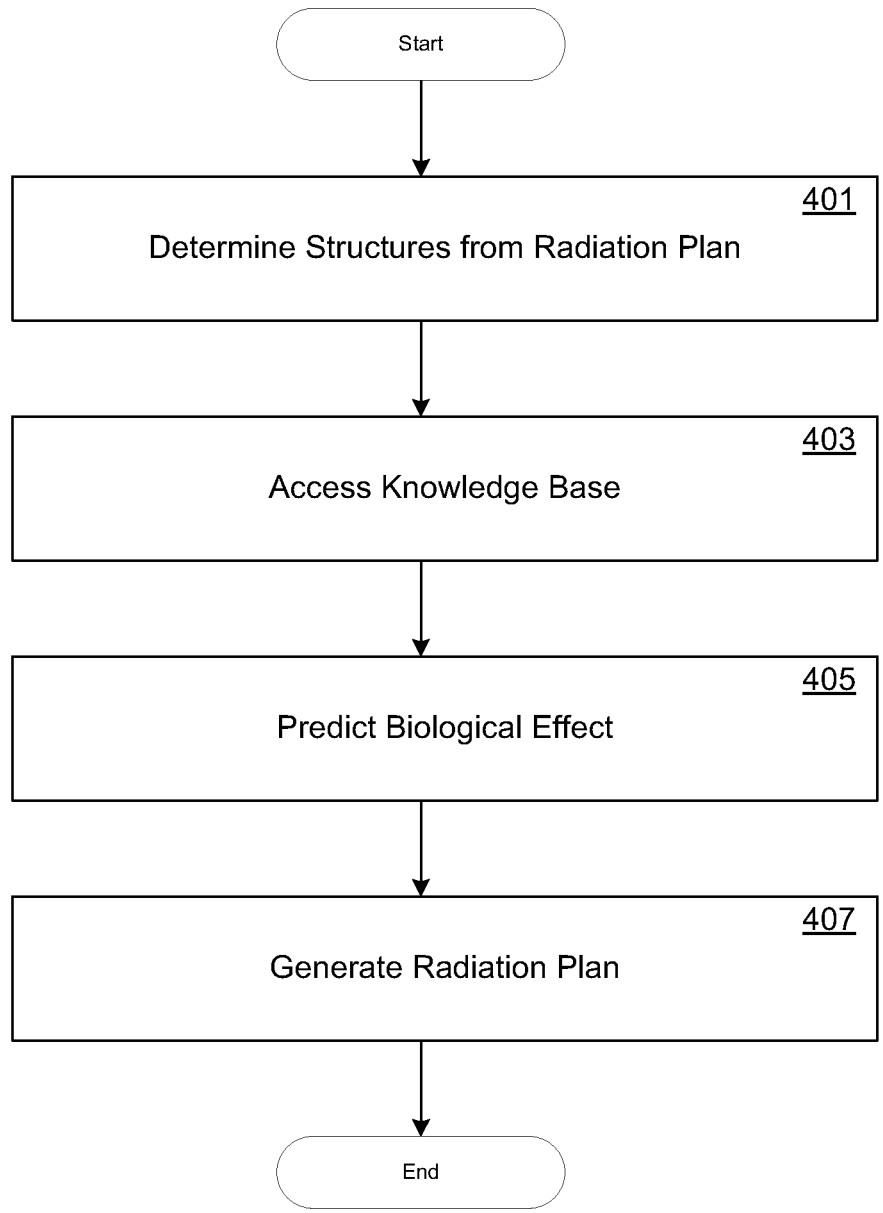
FIG. 4 depicts a flowchart for radiation application planning, in accordance with embodiments of the present disclosure.

FIG. 4 depicts a flow chart 400 of an exemplary process for radiation application planning. Steps 401-407 describe exemplary steps comprising the process 400 depicted in FIG. 4 in accordance with the various embodiments herein described. In one embodiment, the process 400 is implemented at least in part as computer-executable instructions stored in a computer-readable medium and executed in a computing device.

At step 401, structures from a radiation application plan (e.g., a radiation treatment therapy plan) are determined. In one or more embodiments, the radiation application plan may comprise one or more dose distributions of an irradiated beam of particles for a target or treatment patient. The radiation may comprise any of a plurality of radiation modalities, including proton, electron, or photon radiation. According to one or more embodiments, the radiation plan may be pre-generated and associated with the radiation target or patient, and stored as one of a multitude of pre-generated records associated with a corresponding multitude of radiation subjects. In one or more embodiments, the radiation plan includes medical image data corresponding to one or more application sessions. The image data may be generated according to medical imaging techniques including, but not limited to: radiography, magnetic resonance imaging (MRI), ultrasound, elastography, photo-acoustic imaging, thermography, tomography, echocardiography, spectroscopy, and molecular imaging (e.g., positron emission tomography).

In one or more embodiments, at least one organ is also identified from the anatomical structures determined at step 401 from the image data. In one or more embodiments, the structures may be determined (identified), e.g., via manual contouring performed by a technician or specialist (e.g., clinician, radiologist, or oncologist). Alternately, the structures may be automatically determined using automated segmentation techniques (e.g., via reference and comparison to corresponding pre-contoured image data in the knowledge base). In still further embodiments, the structures may be determined according to a combination of manual and automatic contouring. According to one or more embodiments, all or substantially all of the relevant or significant structures (including organs) in the target area may be identified at step 401.

At step 403, a knowledge base is accessed. The knowledge base may be implemented as the knowledge base 302 described above with respect to FIG. 3, and may be communicatively coupled to a computing device executing steps 401-407. In one or more embodiments, accessing the knowledge base may include receiving reference data corresponding to a target area for a session or radiation application/treatment plan. For example, relevant reference data may include data of the same or substantially same target areas in previous clinical applications. According to one or more embodiments, the reference data may also include biological effect data (e.g., biological parameters) that correspond to the biological efficiency of radiation (of the same radiation application modality) for the structures determined at step 401 for the treatment session or plan.

At step 405, target-specific biological effects (e.g., as a function of radiation dosage received) corresponding to the structures determined step 401 are predicted. In one or more embodiments, the biological effects may be predicted by factoring in a dose efficiency model (such as a linear-quadratic model) of one or more biological parameters. These parameters may be user-supplied, or alternately may be pre-calculated (hard-coded) or structure-specific. In still further embodiments, the biological parameters may be pre-calculated in the knowledge base to correspond to a structure or tissue type, and further adjusted dynamically (locally) according to target or patient specific data. For example, patient-specific factors may include relevant background information, additional anatomical or functional information (e.g., obtained from positron emission tomography scanning), patient-specific response to previous treatments or sessions, etc. Exemplary techniques for determining and predicting biological effects are described in greater detail below with respect to FIG. 5.

Finally, at (optional) step 407, a radiation plan (e.g., a dose estimation model) can be generated (or modified) from the biological effect(s) predicted at step 405 using a data model. In one or more embodiments, the radiation plan may be generated by, for example, the prediction model 150 described above with respect to FIG. 2, and/or adjusted in the optimizer 318 described above with respect to FIG. 3.

Figure 5:
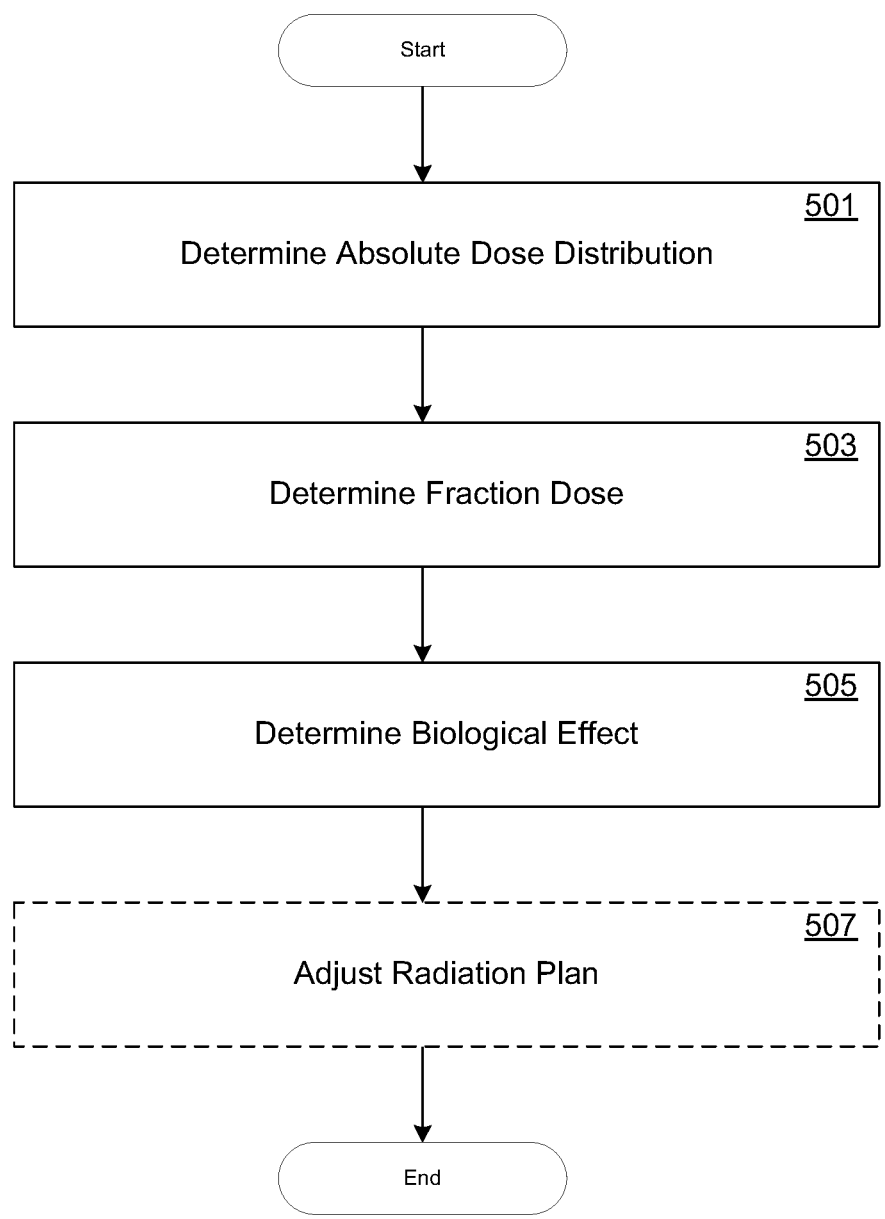
FIG. 5 depicts a flowchart for predicting biological effects, in accordance with embodiments of the present disclosure.

FIG. 5 depicts a flow chart 500 of an exemplary process for determining biological effect of a radiation plan. Steps 501-507 describe exemplary steps comprising the process 500 depicted in FIG. 5 in accordance with the various embodiments herein described. In one embodiment, the process 500 is implemented at least in part as computer-executable instructions stored in a computer-readable medium and executed in a computing device, and may be executed as, for example, step 405 described above with respect to FIG. 4.

At step 501, an absolute dose distribution is determined from a radiation application or treatment plan. The absolute dose distribution may be determined by referencing the radiation application or treatment plan itself, for example. Alternately, the absolute dose distribution may be estimated by referencing corresponding procedures from clinical data (e.g., in a knowledge base) according to one or more data models. At step 503, the fraction dose is determined from the absolute dose distribution determined at step 501. Fraction dose may be calculated simply by dividing the absolute dose distribution by the number of radiation application or treatment sessions corresponding to the radiation application or treatment plan. In one or more embodiments, dose fractionation may be pre-calculated data corresponding to the radiation application or treatment plan. Alternately, the fraction dose may, like the absolute dose distribution, be estimated using a data model by referencing corresponding data from a knowledge base.

At step 505, the biological effect experienced by one or more structures in a target area is determined based on the dose fractionation scheme. For example, the biological efficiency of the radiation can be estimated that factors radiation attenuation factors (as biological parameters) corresponding to the dose fractionation scheme (e.g., dosage per session and session duration). A data model (e.g., a LQ model) is provided the biological efficiency as an additional input and compared to the desired dose distribution. When a difference is observed between the estimated dose distribution that accounts for biological factors and the desired dose distribution, the radiation plan may be adjusted (e.g., by increasing the absolute dosage) in response, to achieve the desired dose distribution (e.g., at step 507). In one or more embodiments, adjustment of the radiation plan may be performed only when the difference between the biological effect corrected estimated dose distribution and the desired dose distribution exceeds a pre-determined threshold.

Exemplary Radiation Application Device

Figure 6:
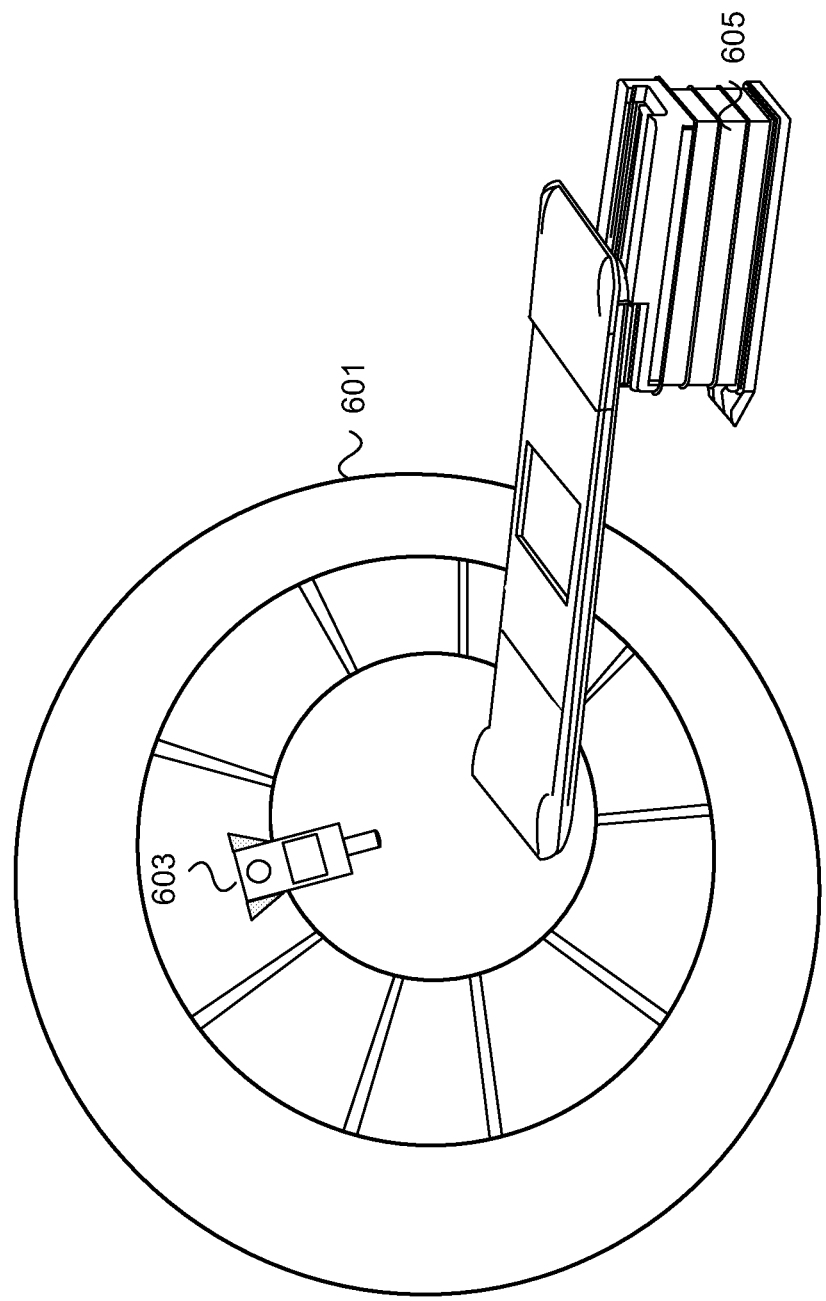
FIG. 6 depicts an exemplary radiation application device, in accordance with embodiments of the present disclosure.

FIG. 6 depicts an exemplary radiation application device 600 in a radiation application room, in accordance with various embodiments of the claimed subject matter. As presented in FIG. 6, radiation application device 600 includes a gantry 601, a radiation treatment nozzle 603, and a subject positioner 605. In one or more embodiments, the gantry 601 may comprise an opening through which at least a portion of the subject positioner 605 is able to enter (e.g., via automatic and/or mechanical means). In one or more embodiments, at least a portion of the gantry may be operable to rotate around the opening (typically while at least a portion of the subject positioner is disposed within). For example, as depicted in FIG. 6, the gantry 601 may be implemented as a ring, at least a portion of which may be rotatable around an axis bisected by the subject positioner 605.

According to one or more embodiments, the gantry 601 is configured to receive irradiated particles (such as protons, electrons, or photons) from a radiation source. In one or more embodiments, the radiation source may be positioned remotely with respect to the treatment therapy room and may be shared between multiple radiation application devices housed in multiple radiation application rooms or suites. Beam lines (e.g., vacuum sealed tubes or pipes used to convey irradiated particles) are used to connect the radiation source to each of the radiation application devices. Once received through the beam line, the irradiated particles are emitted from the radiation application device 600 through a radiation nozzle 603 connected to the gantry 601. In one or more embodiments, the radiation nozzle 603 is rotated about the opening of the gantry 601 through a rotation of at least a portion of the gantry coupled to the radiation nozzle 603. In alternate embodiments, movement of the radiation nozzle 603 may be performed via movement of one or more robotic appendages coupled to the gantry 601.

In one or more embodiments, the subject positioner 605 may include a support structure (such as a table, chair, bench, or bed) upon which a radiation subject may lie, sit, or rest upon. According to further embodiments, portions of the subject positioner 605 may be capable of movement, via automatic and/or mechanical means. For example, the incline of a portion of the resting surface may be increased or decreased (e.g., physically via a mechanism or automatically through a graphical user interface). Portions of the subject positioner 605 may also be equipped with means to rotate, extend, or retract. For example, according to one or more embodiments, a portion of the resting surface of the subject positioner 605 may be extended or physically positioned into an opening of the gantry 601, such that a radiation subject resting on the subject positioner 605 bisects the plane at which the radiation nozzle 603 is directed.

One or both of the gantry 601 and the subject positioner 605 is/are capable of maneuvering, either independently or in conjunction, to align a radiation subject positioned on the subject positioner 605 with the radiation nozzle 603. Movement of the gantry 601 and/or subject positioner 605 may include, but is not limited to, rotation, extension, retraction, contraction, adduction, abduction, etc. of one or more articulated surfaces or portions of the gantry 601, and/or subject positioner 605. In one or more embodiments, radiation nozzle 603 may also be capable of limited movement, via multi-axial rotation or extension of one or more portions, for example. Movement of the gantry 601, radiation nozzle 603, and/or subject positioner 605 may be performed automatically, via pre-programmed instructions that correspond to optimized alignments for desired iso-centers, or may be controlled remotely via a user interface.

A radiation subject may be positioned (e.g., by lying prone) on a subject positioner 605 at an initial or starting position. One or more portions of the subject positioner 605 may extend towards an opening presented by the gantry 601, such that a target area of the radiation subject is aligned with a position of the radiation nozzle 603, located on or around an inner surface of the gantry 601. In alternate or further embodiments, the gantry 601 may also rotate in an arc around the circumference of the gantry 601 to position the radiation nozzle 603 to produce the desired beam field or to do position verification of a radiation subject positioned on a subject positioner 605. Once the gantry 601, radiation nozzle 603, and/or subject positioner 605 are aligned in the desired orientation, radiation application may begin. Specifically, an iso-center in the radiation subject may be aligned with the radiation nozzle 603 via movement of the gantry 601 and/or subject positioner 605. In one or more embodiments, radiation application may comprise the application of irradiated particles generated at a (remote) particle accelerator, received in the gantry 601, and emitted at an iso-center located in a radiation subject according to a pre-determined radiation application plan.

By utilizing the systems and methods described above, the application of irradiated particles can be applied to a radiation subject that more accurately conforms to a radiation plan by accounting for structure-specific biological effects maintained in a knowledge base. By incorporating biological data and fraction dose information, dose-estimation models can be created and trained to more accurately estimate dose absorption and effectiveness. Moreover, existing estimation models may be adapted to create dose estimations that account for the biological efficiency of target structures. According to one or more embodiments, the biological estimates generated by the systems and methods described above may also be converted back to dose-distribution estimates using the fraction dose information in combination with the structure-specific parameters.

The biologically corrected dose-estimates achieved by the solutions described above may be used to create variable daily dose estimates when fractionation schemes include breaks or partial treatments. Existing estimation models may also be used in conjunction with predicted biological effects to determine optimal fractionation schemes.

Although the subject matter has been described in language specific to structural features and/or processological acts, it is to be understood that the subject matter defined in the appended claims is not necessarily limited to the specific features or acts described above. Rather, the specific features and acts described above are disclosed as example forms of implementing the claims.

What is claimed is:

1. A system comprising:
    a memory device configured to store at least a set of programmed instructions and a radiation plan data;
    a network connection communicatively coupling the system with a network; and
    a processor configured to execute the set of programmed instructions to predict a radiation-target-specific biological effect for a radiation target, the processor being further configured to determine a plurality of structures in image data corresponding to the radiation target, identify at least one organ from the plurality of structures, access a knowledge base via the network connection to determine reference data comprising at least one biological characteristic corresponding to the at least one organ, and predict the radiation-target specific biological effect for the plurality of structures based on the at least one biological characteristic of the at least one organ;
    wherein the at least one biological characteristic comprises at least one of: a recovery rate corresponding to at least one structure of the plurality of structures; a repopulation rate corresponding to at least one structure of the plurality of structures; a re-distribution rate corresponding to at least one structure of the plurality of structures; a re-oxygenation rate corresponding to at least one structure of the plurality of structures; and a radio resistance rate corresponding to at least one structure of the plurality of structures;
    wherein the processor is further configured to generate a radiation plan based on the predicted biological effect;
    wherein the processor is further configured to generate instructions to a radiation application device coupled to a radiation source, the instructions comprising instructions to apply radiation to the radiation target according to the radiation plan.

2. The system of claim 1, wherein, to predict the biological effect, the processor is further configured to determine an absolute dose distribution from the radiation plan.

3. The system of claim 1, wherein the radiation plan comprises a plan to apply the radiation according to a plurality of fractionations.

4. The system of claim 1, wherein, to predict the biological effect, the processor is further configured to determine an absolute dose distribution from the radiation plan, to determine a fraction dose based on the absolute dose distribution and a plurality of fractionations, and to determine the biological effect based on the at least one biological characteristic and corresponding to the plurality of fractionations.

5. The system of claim 1, wherein, to predict the biological effect, the processor is further configured to determine an absolute dose distribution from the radiation plan, and to determine a fraction dose based on the absolute dose distribution and a plurality of fractionations.

6. The system of claim 1, wherein, the generate the radiation plan, the processor is further configured to plot a dose-volume histogram (DVH) curve.

7. The system of claim 1, wherein, the generate the radiation plan, the processor is further configured to plot a dose-volume histogram (DVH) curve for each structure of the plurality of structures based on a radiation dose adjusted to account for the predicted biological effect.

8. The system of claim 1, wherein, to predict the biological effect, the processor is further configured to factor at least one of:
    a user-supplied biological effect parameter; and
    a pre-determined biological effect parameter.

9. The system of claim 1, wherein the radiation application device comprises a gantry.

10. The system of claim 1, wherein the radiation comprises proton radiation, electron radiation, or photon radiation.

11. A system comprising:
    a memory device configured to store at least a set of programmed instructions and a radiation plan data;

a network connection communicatively coupling the system with a network; and a processor configured to execute the set of programmed instructions to predict a radiation-target-specific biological effect for a radiation target, the processor being further configured to determine a plurality of structures in image data corresponding to the radiation target, identify at least one organ from the plurality of structures, access a knowledge base via the network connection to determine reference data comprising at least one biological characteristic corresponding to the at least one organ, predict the radiation-target specific biological effect for the plurality of structures based on the at least one biological characteristic of the at least one organ, and generate a radiation plan based on the predicted biological effect;

wherein the at least one biological characteristic comprises at least one of: a recovery rate corresponding to at least one structure of the plurality of structures; a repopulation rate corresponding to at least one structure of the plurality of structures; a re-distribution rate corresponding to at least one structure of the plurality of structures; a re-oxygenation rate corresponding to at least one structure of the plurality of structures; and a radio resistance rate corresponding to at least one structure of the plurality of structures;

wherein the processor is configured to apply a data model to the at least one biological characteristic to predict the biological effect; and wherein the processor is further configured to generate instructions to a radiation application device coupled to a radiation source, the instructions comprising instructions to apply radiation to the radiation target according to the radiation plan.

12. The system of claim 11, wherein the data model comprises a linear-quadratic (LQ) data model.

13. The system of claim 11, wherein, to the generate the radiation plan, the processor is further configured to plot a dose-volume histogram (DVH) curve for each structure of the plurality of structures based on a radiation dose adjusted to account for the predicted biological effect.

14. The system of claim 11, wherein the radiation plan comprises a plan to apply the radiation according to a plurality of fractionations.

15. The system of claim 11, wherein, to generate the radiation plan, the processor is further configured to plot a dose-volume histogram (DVH) curve.

16. The system of claim 11, wherein, to predict the biological effect, the processor is further configured to factor at least one of:
a user-supplied biological effect parameter; and
a pre-determined biological effect parameter.

17. A system comprising:
a memory device configured to store at least a set of programmed instructions and a radiation plan data;
a network connection communicatively coupling the system with a network; and
a processor configured to execute the set of programmed instructions to predict a radiation-target-specific biological effect for a radiation target, the processor being further configured to determine a plurality of structures in image data corresponding to the radiation target, identify at least one organ from the plurality of structures, access a knowledge base via the network connection to determine reference data comprising at least one biological characteristic corresponding to the at least one organ, predict the radiation-target specific biological effect for the plurality of structures based on the at least one biological characteristic of the at least one organ, and generate a radiation plan based on the predicted biological effect;

wherein the at least one biological characteristic comprises at least one of: a recovery rate corresponding to at least one structure of the plurality of structures; a repopulation rate corresponding to at least one structure of the plurality of structures; a re-distribution rate corresponding to at least one structure of the plurality of structures; a re-oxygenation rate corresponding to at least one structure of the plurality of structures; and a radio resistance rate corresponding to at least one structure of the plurality of structures;

wherein the processor is configured to factor a structure-based biological effect parameter to predict the biological effect; and wherein the processor is further configured to generate instructions to a radiation application device coupled to a radiation source, the instructions comprising instructions to apply radiation to the radiation target according to the radiation plan.

18. The system of claim 17, wherein the radiation plan comprises a plan to apply the radiation according to a plurality of fractionations.

19. The system of claim 17, wherein the processor is configured to apply a data model to the at least one biological characteristic to predict the biological effect.

20. The system of claim 19, wherein the data model comprises a linear-quadratic (LQ) data model.

* * * * *